United States Patent [19]

Cimarusti et al.

[11] 4,116,978
[45] Sep. 26, 1978

[54] D-HOMO OXASTEROIDS

[75] Inventors: Christopher M. Cimarusti, Hamilton Square; Paul Grabowich, New Brunswick; Ravi K. Varma, Belle Mead, all of N.J.

[73] Assignee: E. R. Squibb & Sons, Inc., Princeton, N.J.

[21] Appl. No.: 817,315

[22] Filed: Jul. 20, 1977

[51] Int. Cl.$^2$ .................. C07D 311/02; A61K 31/35
[52] U.S. Cl. .................................. 260/345.2; 424/283
[58] Field of Search .................................... 260/345.2

[56] References Cited

U.S. PATENT DOCUMENTS

| | | | |
|---|---|---|---|
| 2,832,772 | 4/1958 | Farrar et al. | 260/345.2 |
| 3,294,819 | 12/1966 | Krakower et al. | 260/345.2 |
| 3,467,677 | 9/1969 | Gardner | 260/345.2 |

OTHER PUBLICATIONS

Iriarte et al., J.C.S. Chem. Comm., 1110 (1972).
Kuo et al., J. Org. Chem., 28, 1619 (1963).

Primary Examiner—Nicky Chan
Attorney, Agent, or Firm—Lawrence S. Levinson; Merle J. Smith; Donald J. Barrack

[57] ABSTRACT

Steroids having the formula

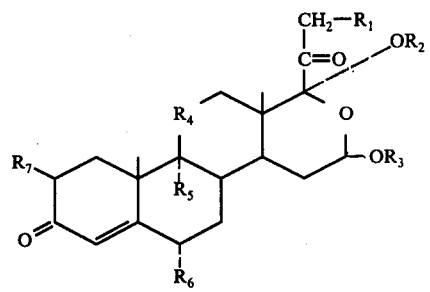

or the 1,2-dehydro derivative thereof, wherein $R_1$ is hydrogen, acyloxy, halogen, or hydroxy; $R_2$ is hydrogen or alkyl; $R_3$ is alkyl; $R_4$ is carbonyl, $\beta$-hydroxymethylene, $\beta$-chloromethylene or $\beta$-bromomethylene; $R_5$ is hydrogen, fluorine, chlorine or bromine; $R_6$ is hydrogen, fluorine or methyl; and $R_7$ is hydrogen, chlorine or bromine; can be used as antiinflammatory agents.

25 Claims, No Drawings

D-HOMO OXASTEROIDS

BACKGROUND OF THE INVENTION

German Offenlegungsschrift No. 2,526,788 published Dec. 23, 1976 discloses that the oxidation of certain 17-alkanoyloxy-$\Delta^{16}$-steroids with osmium tetroxide opens the D-ring of the steroids yielding a 16,17-seco-steroid of the type

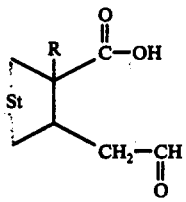

wherein "St" symbolizes A, B and C rings of the steroid and R symbolizes methyl or ethyl. Ring closure of the 16,17-seco-steroid pictured above yields a D-homo-oxasteroid of the type

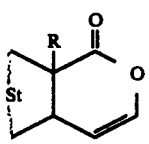

Subsequent treatment of the 17-oxa-17a-oxo-D-homo-steroid yields a steroid of the type

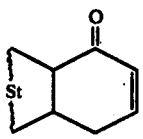

Ozonolysis of certain 17-acetoxy-$\Delta^{16}$-estrenes followed by ring closure (using p-toluenesulfonic acid) of the resulting seco-steroids, is taught by Baran in U.S. Pat. No. 3,257,412 to yield 17-oxo-D-homoestrenes.

Iriarte et al., *J. C. S. Chem. Comm.*, 1110 (1972), describe the osmium tetroxide oxidation and subsequent periodic oxidation of the enol acetate having the structure

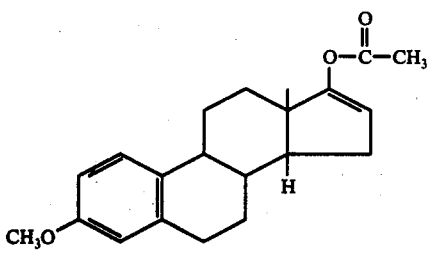

to yield a compound having the structure

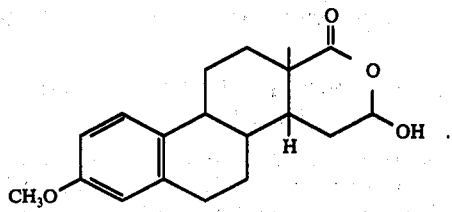

Kuo et al., *J. Org. Chem.*, 28, 1619 (1963), describe the preparation of a 17-oxa-D-homopregnane having the structure

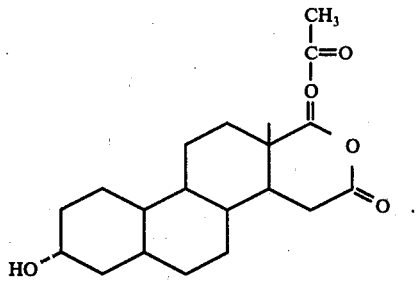

SUMMARY OF THE INVENTION

Steroids having the formula

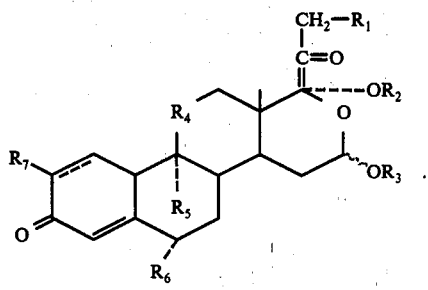

can be used as antiinflammatory agents.

In formula I, and throughout the specification, the symbols are as defined below:

$R_1$ is hydrogen, acyloxy (i.e.,

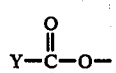

wherein Y is alkyl or aryl), halogen or hydroxy;
$R_2$ is hydrogen or alkyl;
$R_3$ is alkyl;
$R_4$ is carbonyl, $\beta$-hydroxymethylene, $\beta$-chloromethylene, or $\beta$-bromomethylene;
$R_5$ is hydrogen, fluorine, chlorine or bromine;
$R_6$ is hydrogen, fluorine or methyl; and
$R_7$ is hydrogen, chlorine or bromine; with the proviso that if $R_1$ is hydroxy, $R_2$ is alkyl; and with the further proviso that if $R_2$ is alkyl, it is the same alkyl group as $R_3$. A dotted line in the 1,2 position of a structural formula in this disclosure indicates the optional presence of ethylenic unsaturation.

The term "aryl", as used throughout the specification, refers to phenyl or phenyl substituted with one or two alkyl, alkoxy or halogen groups.

The term "halogen", as used throughout the specification, refers to fluorine, chlorine, bromine or iodine.

The terms "alkyl" and "alkoxy", as used throughout the specification, refer to groups having 1 to 10 carbon atoms.

DETAILED DESCRIPTION OF THE INVENTION

The D-homo oxasteroids of this invention, wherein $R_1$ is hydrogen, acyloxy or halogen (this subgrouping of substituents is hereinafter referred to as "$R'_1$") and $R_2$ is hydrogen, can be prepared by reacting the corresponding $\Delta^{16}$-pregnene having the formula

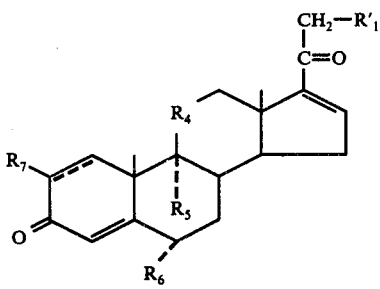

with ozone, and an alkanol having the formula

$R_3$—OH, (III)

and then treating the reaction mixture with a reducing agent, e.g., a dialkylsulfide such as dimethylsulfide, in an organic solvent, e.g., a halogenated hydrocarbon such as dichloromethane. The steroid product has the formula

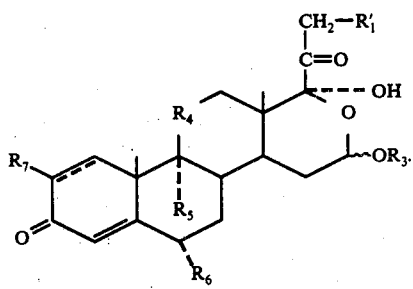

The above-described reaction is a novel one, and as such, it constitutes an integral part of this invention.

Reaction of a steroid product of formula IV with an alkanol in the presence of an acid catalyst, e.g., p-toluene-sulfonic acid, yields the corresponding product having the formula

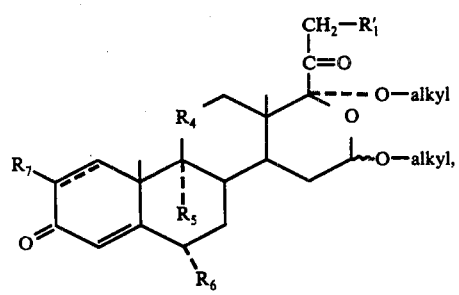

if carried out at an elevated temperature, preferably under reflux conditions.

Saponification of a steroid of formula V, wherein $R'_1$ is acyloxy, yields the corresponding 21-hydroxy steroid having the formula

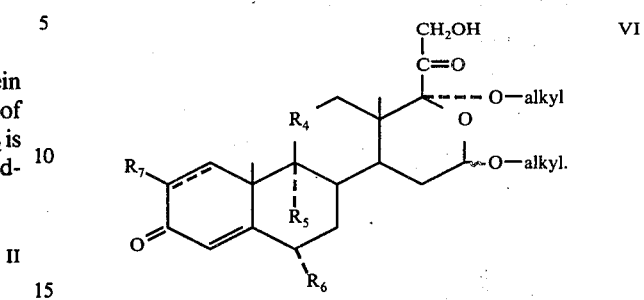

The saponification reaction is run in the presence of a base, e.g., an alkali metal carbonate, and can be carried out in an organic solvent, e.g., an alkanol.

Many alternative processes are available for the preparation of the steroids of this invention. For example, the steroids of formula I having a halogen substituent in the 21-position can be prepared from the corresponding 21-hydroxy steroids via the 21-mesylate. Another example involves the trans-etherification of a steroid of formula IV. In some instances, a steroid of formula IV, especially one with a large, sterically hindered $R_3$ group (e.g., isopropyl or t-butyl) can be prepared by reacting a steroid of formula IV with the appropriate alkanol, in the presence of an acid catalyst at room temperature.

Steroids having the formula

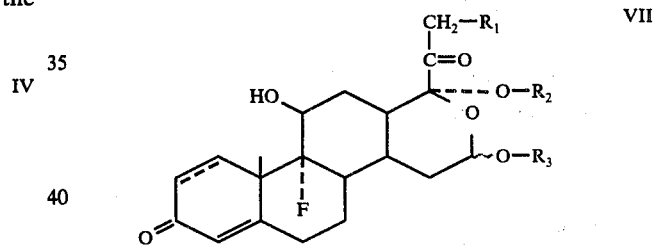

are contemplated as a sub-genus within the broader genus of formula I.

In some instances, the preparation of the steroids of formula I will yield a solvate of the steroid, rather than the steroid per se. These solvates are also contemplated as a part of this invention.

The steroids of formula I can be used in lieu of known glucocorticoids in the treatment of inflammatory conditions; e.g., rheumatoid arthritis. They can be administered in the same manner as hydrocortisone, the dosage being adjusted for the relative potency of the particular steroid. Additionally, the steroids of this invention can be used topically in lieu of known glucocorticoids in the treatment of skin conditions such as dermatitis, psoriasis, sunburn, neurodermatitis, eczema or anogenital pruritus.

When given orally, the steroids of this invention may be used in a dosage range of 0.1 to 200 milligrams, preferably 0.3 to 100 milligrams, for a 70 kg. mammal. If administered topically, the steroids of this invention may be used in the range of 0.01 to 5.0% by weight, preferably 0.05 to 2.0% by weight, in a conventional cream, ointment, lotion or the like.

The following examples are specific embodiments of this invention.

EXAMPLE 1

21-(Acetyloxy)-9-fluoro-11β,17a-dihydroxy-16β-methoxy-D-homo-17-oxapregna-1,4-diene-3,20-dione A solution of 805 mg of 21-(acetyloxy)-9-fluoro-11β-hydroxypregna-1,4,16-triene-3,20-dione in 30 ml of 2:1 dichloromethane-methanol is cooled to −78° C. and a stream of ozone in oxygen passed through (0.00225 moles). An amount of 2 ml (large excess) of dimethylsulfide is added, the solution is kept for 2 hours at ambient temperature and the solvents are then evaporated in vacuo. A solution of the residue in chloroform is washed with water, dried, and chromatographed on a 60 g-silica gel column. Elution with 3:1 chloroform-ethyl acetate gives 605 mg of crude product that crystallizes from acetone-hexane to give 340 mg of material, melting point 170°–172° C., dec. Two recrystallizations from methanol give 195 mg of product, melting point 170°–172° C., dec.

Anal. Calc'd. for $C_{24}H_{31}FO_8$: C, 61.78; H, 6.69; F, 4.07.

Found: C, 62.00; H, 6.90; F, 4.25.

EXAMPLE 2

21-Chloro-9-fluoro-11β,17a-dihydroxy-16β-methoxy-D-homo-17-oxapregn-4-ene-3,20-dione A solution of 1.36 g of 21-chloro-9-fluoro-11β-hydroxypregna-4,16-diene-3,20-dione in 30 ml of 2:1 dichloromethane-methanol is cooled to −78° C. and a stream of ozone in oxygen (0.00397 mole) passed through for 11 minutes. Several milliliters (large excess) of dimethylsulfide are added and the solution is allowed to warm to ambient temperature. After 210 minutes, the solvents are removed in vacuo and the residue dissolved in chloroform, washed with water, dried and applied on a 40 g-silica gel column. Elution with chloroform gives 1.03 g of product that crystallizes from methanol to give 400 mg of solid in two crops. A further recrystallization from methanol gives 304 mg of product, melting point 160°–162° C., dec.

Anal. Calc'd. for $C_{22}H_{30}ClFO_6$: C, 59.39; H, 6.80; Cl, 7.97; F, 4.27.

Found: C, 59.49; H, 7.00; Cl, 8.06; F, 4.00.

EXAMPLE 3

21-(Acetyloxy)-9-fluoro-11β,17a-dihydroxy-16β-methoxy-D-homo-17-oxapregn-4-ene-3,20-dione, methanol solvate (1:1)

A solution of 5.0 g of 21-(acetyloxy)-9-fluoro-11β-hydroxypregna-4,16-diene-3,20-dione in a mixture of 100 ml of dichloromethane and 40 ml of methanol is cooled to −78° C. and a stream of ozone in oxygen (0.0133 mole) passed through. The solution is treated with 5 ml of dimethylsulfide and allowed to warm to ambient temperature. The solvents are removed in vacuo and a solution of the residue in chloroform is washed with water, dried, and chromatographed on a 50 g-silica gel column. Elution with chloroform gives 4.7 g of material which crystallizes from methanol to give 2.13 g of substantially pure material. Two recrystallizations of 1 g of this material give 705 mg of the title methanol solvate.

Anal. Calc'd. for $C_{25}H_{37}FO_9$: C, 59.98; H, 7.45; F, 3.79.

Found: C, 59.37; H, 7.55; F, 3.79.

EXAMPLE 4

21-(Acetyloxy)-16β,17a-diethoxy-9-fluoro-11β-hydroxy-D-homo-17-oxapregn-4-ene-3,20-dione A solution of 1.615 g of 21-(acetyloxy)-9-fluoro-11β,17a-dihydroxy-16β-methoxy-D-homo-17-oxapregn-4-ene-3,20-dione, methanol solvate (1:1) (see Example 3) in 50 ml of ethanol is refluxed with 100 mg of p-toluenesulfonic acid for 1 hour, cooled, and diluted with water. The resulting solution is extracted with chloroform, and the chloroform extract washed with 5% sodium bicarbonate solution and water, dried, and evaporated. The residue is dissolved in chloroform and chromatographed on a 50 g-silica gel column. Elution with chloroform gives 1.37 g of material which crystallizes from ether-hexane to give 785 mg of product, melting point 220°–222° C.

Anal. Calc'd. for $C_{27}H_{39}FO_8$: C, 63.51; H, 7.70; F, 3.72.

Found: C, 63.77; H, 7.80; F, 3.46.

EXAMPLE 5

16β,17a-Diethoxy-9-fluoro-11β,21-dihydroxy-D-homo-17-oxapregn-4-ene-3,20-dione A solution of 378 mg of 21-(acetyloxy)-16β,17a-diethoxy-9-fluoro-11β-hydroxy-D-homo-17-oxapregn-4-ene-3,20-dione (see Example 4) in 15 ml of methanol is stirred at 0° C. with 1.5 ml of 10% potassium carbonate solution under nitrogen for 1 hour; stirred 1 hour at room temperature; and stirred 30 minutes at 70° C. The resulting solution is cooled, diluted with water and extracted with chloroform. The chloroform solution is dried and evaporated to give 291 mg of the title compound.

EXAMPLE 6

21-Chloro-16β,17a-diethoxy-9-fluoro-11β-hydroxy-D-homo-17-oxapregn-4-ene-3,20-dione (A)

16β,17a-Diethoxy-9-fluoro-11β-hydroxy-21-(mesyloxy)-D-homo-17-oxapregn-4-ene-3,20-dione A solution of 740 mg of 16β,17a-diethoxy-9-fluoro-11β,21-dihydroxy-D-homo-17-oxapregn-4-ene-3,20-dione (see Example 5) in 10 ml of pyridine is stirred at 0° C. with 0.2 ml of methanesulfonyl chloride for 2 hours. The solution is poured into cold 2N hydrochloric acid and the resulting solid filtered. Attempted purification by preparative thin-layer chromatography (TLC) fails. The resulting 601 mg of material is dissolved in pyridine and stirred for about 16 hours with excess methanesulfonyl chloride at 5° C. After workup as above (see Example 5) the solid is dissolved in chloroform and chromatographed on a 40 g-silica gel column. Elution with chloroform gives 361 mg of TLC pure mesylate.

(B)

21-Chloro-16β,17a-diethoxy-9-fluoro-11β-hydroxy-D-homo-17-oxapregn-4-ene-3,20-dione A solution of 361 mg of the above mesylate in 25 ml of dimethylformamide is refluxed with 3.0 g of lithium chloride for 30 minutes under nitrogen. The solution is cooled to room temperature, diluted with water, and the resulting solid filtered. The solid is dissolved in chloroform and chromatographed on a 20 g-silica gel column. Elution with chloroform gives 175 mg of material which crystallizes from methanol to give 123 mg of TLC pure material, melting point 206°–208° C., dec.

Anal. Calc'd. for $C_{25}H_{36}ClFO_6$: C, 61.65; H, 7.45; Cl, 7.28; F, 3.90.

Found: C, 61.85; H, 7.62; Cl, 7.17; F, 4.18.

EXAMPLE 7

21-Chloro-16β-ethoxy-9-fluoro-11β,17a-dihydroxy-D-homo-17-oxapregna-1,4-diene-3,20-dione A solution of 1.9 g of 21-chloro-9-fluoro-11β-hydroxy-pregna-1,4,16-triene-3,20-dione in 100 ml of dichloromethane and 50 ml of ethanol is cooled to −78° C. and a 10% excess of ozone in oxygen passed through. The solution is treated with 5 ml of dimethylsulfide and allowed to warm to ambient temperature and stand for about 16 hours. The solvents are evaporated and a chloroform solution of the residue is washed with water, dried, and evaporated. The residue is dissolved in chloroform and chromatographed on a 40 g-silica gel column. Elution with chloroform and then chloroform-ethyl acetate (5:1) gives TLC pure material that crystallizes from methanol-dichloromethane to give 563 mg, melting point 171°–173° C.

Anal. Calc'd. for $C_{23}H_{30}ClFO_6$: C, 60.45; H, 6.62; Cl, 7.76; F, 4.12.

Found: C, 60.34; H, 6.60; Cl, 7.62; F, 4.37.

EXAMPLE 8

21-Chloro-9-fluoro-11β,17a-dihydroxy-16β-methoxy-D-homo-17-oxapregna-1,4-diene-3,20-dione A solution of 1.9 g of 21-chloro-9-fluoro-11β-hydroxypregna-1,4,16-triene-3,20-dione in 100 ml of dichloromethane and 50 ml of methanol is cooled to −78° C. and a 10% excess of ozone in oxygen passed through. After addition of 5 ml of dimethylsulfide the solution is allowed to warm to room temperature and stirred for about 16 hours. The solvents are removed in vacuo and an ethyl acetate solution of the residue is washed with water, dried, and evaporated to give a solid. Recrystallization from methanol-dichloromethane gives 925 mg of product, melting point 181°–183° C.

Anal. Calc'd. for $C_{22}H_{28}ClFO_6$: C, 59.66; H, 6.37; Cl, 8.06; F. 4.29.

Found: C, 59.78; H, 6.62; Cl, 7.82; F, 4.51.

EXAMPLE 9

21-Chloro-16β,17a-diethoxy-9-fluoro-11β-hydroxy-D-homo-17-oxapregna-1,4diene-3,20-dione A solution of 787 mg of 21-chloro-16β-ethoxy-9-fluoro-11β,17a-dihydroxy-D-homo-17-oxapregna-1,4-diene-3,20-dione (see Example 7) in 50 ml of ethanol is refluxed with 100 mg of p-toluene-sulfonic acid for 1 hour. The solution is cooled, poured into 450 ml of water, stirred for 15 minutes, and filtered. The resulting solid is recrystallized from methanol-dichloromethane to give 550 mg of product, melting point 218°–220° C., dec.

Anal. Calc'd. for $C_{25}H_{34}ClFO_6$: C, 61.91; H, 7.07; Cl, 7.31; F, 3.92.

Found: C, 62.20; H, 7.21; Cl, 7.13; F, 4.16.

EXAMPLE 10

21-Chloro-9-fluoro-11β-hydroxy-16β,17a-dimethoxy-D-homo-17-oxapregna-1,4-diene-3,20-dione A solution of 1.314 g of 21-chloro-9-fluoro-11β,17a-dihydroxy-16β-methoxy-D-homo-17-oxapregna-1,4-diene-3,20-dione (see Example 7) in 50 ml of methanol is refluxed for 90 minutes with 100 mg of p-toluenesulfonic acid. The solution is poured into cold water and extracted with ethyl acetate to give the crude product. Crystallization from methanol-dichloromethane gives 582 mg of product, melting point 228°–230° C., dec.

Anal. Calc'd. for $C_{23}H_{30}ClFO_6$: C, 60.45; H, 6.62; Cl, 7.76; F, 4.12.

Found: C, 60.49; H, 6.64; Cl, 7.86; F, 4.26.

EXAMPLE 11

21-(Acetyloxy)-16β-ethoxy-9-fluoro-11β,17a-dihydroxy-D-homo-17-oxapregna-1,4-diene-3,20-dione A solution of 4.02 g of 21-(acetyloxy)-9-fluoro-11β-hydroxypregna-1,4,16-triene-3,20-dione in 100 ml of dichloromethane and 50 ml of ethanol is cooled to −78° C. and a 10% excess of ozone in oxygen is passed through. After addition of 5 ml of dimethylsulfide the solution is allowed to warm to room temperature over about a 16-hour period. The solvents are evaporated and a solution of the residue in ethyl acetate is washed with water, dried, and evaporated. Crystallization from ethanol-dichloromethane gives 2.72 g of material, melting point 168°–170° C., dec.

Anal. Calc'd. for $C_{25}H_{33}FO_8$: C, 62.49; H, 6.92; F, 3.95.

Found: C, 62.55; H, 6.92; F, 3.88.

EXAMPLE 12

21-(Acetyloxy)-16β,17a-diethoxy-9-fluoro-11β-hydroxy-D-homo-17-oxapregna-1,4-diene-3,20-dione A solution of 1.2 g. of 21-(acetyloxy)-16β-ethoxy-9-fluoro-11β,17a-dihydroxy-D-homo-17-oxapregna-1,4-diene-3,20-dione (see Example 11) in 50 ml of ethanol is refluxed for 90 minutes with 100 mg of p-toluenesulfonic acid. The mixture is cooled, poured into ice-water and extracted with ethyl acetate to give 1.0 g of solid. This is combined with 1.2 g of similar material, dissolved in chloroform and chromatographed on a 60 g-silica gel column. Elution with chloroform gives 1.75 g of TLC pure solid. Crystallization from methanol-dichloromethane gives 1.35 g of product, melting point 223°–225° C. (foams and resolidifies at 120° C.).

Anal. Calc'd. for $C_{27}H_{37}FO_8$: C, 63.76; H, 7.33; F, 3.74.

Found: C, 63.61; H, 7.10; F, 3.92.

EXAMPLE 13

21-(Acetyloxy)-9-fluoro-11β-hydroxy-16β,17a-dimethoxy-D-homo-17-oxapregna-1,4-diene-3,20-dione A solution of 5.15 g of 21-(acetyloxy)-9-fluoro-11β,17a-dihydroxy-16β-methoxy-D-homo-17-oxapregna-1,4-diene-3,20-dione (see Example 1) in 100 ml of methanol is refluxed for 90 minutes with 200 mg of p-toluenesulfonic acid. The solution is poured into water and the resulting solid filtered. The solid is dissolved in dichloromethane, dried, and chromatographed on a 60 g-silica gel column. Elution with chloroform gives 2.1 g of material which is a mixture of isomers by tlc and nmr. This material is crystallized from acetone-hexane to give 738 mg of a mixture. The mother liquor is evaporated and crystallized from methanol twice to give 455 mg of product, melting point 225°–227° C.

Anal. Calc'd. for $C_{25}H_{33}FO_8$: C, 62.49; H, 6.92; F, 3.95.

Found: C, 62.41; H, 7.04; F, 4.20.

EXAMPLE 14

21-Chloro-16β-(1,1-dimethylethoxy)-9-fluoro-11β,17a-dihydroxy-D-homo-17-oxapregna-1,4-diene-3,20-dione A solution of 1.9 g of 21-chloro-9-fluoro-11β-hydroxy-pregna-1,4,16-triene-3,20-dione in 120 ml of dichloromethane and 30 ml of t-butanol is cooled to −78° C. and a 10% excess of ozone in oxygen passed through. After addition of 5 ml of dimethylsulfide the solution is allowed to warm to room temperature and stirred for about 16 hours. The solvents are removed in vacuo and the residue dissolved in ethyl acetate, washed with water, dried, and evaporated. The residue is dissolved in chloroform and chromatographed on a 20 g-silica gel column. Elution with chloroform gives 1.15 g of material. Several crystallizations from methanol-dichloromethane give 365 mg of product, melting point 170°–173° C.

Anal. Calc'd. for $C_{25}H_{34}ClFO_6$: C, 61.91; H, 7.07; Cl, 7.31; F, 3.92. Found: C, 61.79; H, 7.37; Cl, 7.02; F, 3.95.

EXAMPLE 15

21-Chloro-9-fluoro-11β-hydroxy-16β,17a-bis-(1-methylethoxy)-D-homo-17-oxapregna-1,4-diene-3,20-dione A solution of 1.85 g of 21-chloro-16β-ethoxy-9-fluoro-11β,17a-dihydroxy-D-homo-17-oxapregna-1,4-diene-3,20-dione (see Example 7) in 50 ml of isopropanol is refluxed for 30 minutes with 180 mg of p-toluenesulfonic acid. The solution is diluted with water and extracted with ethyl acetate to give the crude product. This is dissolved in chloroform and chromatographed on a silica gel column to give 713 mg of the title compound after crystallization from methanol. This is combined with 545 mg of similar material for characterization; melting point 195°–197° C., dec.

Anal. Calc'd. for $C_{27}H_{38}ClFO_6$: C, 63.21; H, 7.47; Cl, 6.91; F, 3.70. Found: C, 63.25; H, 7.69; Cl, 6.81; F, 3.99.

EXAMPLE 16

21-Chloro-9-fluoro-11β,17a-dihydroxy-16β-(1-methylethoxy)-D-homo-17-oxapregna-1,4-diene-3,20-dione A solution of 1.63 g of 21-chloro-16β-ethoxy-9-fluoro-11β,17a-dihydroxy-D-homo-17-oxapregna-1,4-diene-3,20-dione (see Example 7) in 400 ml of isopropanol is stirred for 3.5 days with 500 mg of p-toluenesulfonic acid. The solution is poured into 2 liters of water and extracted with ethyl acetate to give 1.61 g of solid. This is triturated with dichloromethane and filtered to give 782 mg of TLC pure material. The filtrate is chromatographed on a 30 g-silica gel column to give a further 400 mg. These are combined and recrystallized from methanol to give 844 mg of product, melting point 238°–240° C.

Anal. Calc'd. for $C_{24}H_{32}ClFO_6$: C, 61.34; H, 6.65; Cl, 7.55; F, 4.04. Found: C, 61.54; H, 6.93; Cl, 7.37; F, 4.19.

EXAMPLES 17–24

Following the procedures of Example 1, but substituting the steroid listed in column I for 21-(acetyloxy)-9-fluoro-11β-hydroxypregn-1,4,16-triene-3,20-dione yields the steroid listed in column II.

| Column I | Column II |
|---|---|
| 21-(acetyloxy)-6α,9-difluoro-11β-hydroxy-pregna-1,4,16-triene-3,20-dione | 21-(acetyloxy)-6α,9-difluoro-11β,17a-dihydroxy-16β-methoxy-D-homo-17-oxapregna-1,4-diene-3,20-dione |
| 9-fluoro-11β-hyroxy-6α-methylpregna-1,4,16-triene-3,20-dione | 9-fluoro-11β,17a-dihydroxy-16β-methoxy-6α-methyl-D-homo-17-oxapregna-1,4-diene-3,20-dione |
| 11β-hydroxypregna-4,16-diene-3,20-dione | 11β,17a-dihydroxy-16β-methoxy-D-homo-17-oxapregn-4-ene-3,20-dione |
| 21-(acetyloxy)-2-chloro-6α,9-difluoro-11β-hydroxypregna-1,4,16-triene-3,20-dione | 21-(acetyloxy)-2-chloro-6α,9-difluoro-11β,17a-dihydroxy-16β-methoxy-D-homo-17-oxapregna-1,4-diene-3,20-dione |
| 21-(acetyloxy)-2-bromo-6α,9-difluoro-11β-hydroxypregna-1,4,16-triene-3,20-dione | 21-(acetyloxy)-2-bromo-6α,9-difluoro-11β,17a-dihydroxy-16β-methoxy-D-homo-17-oxapregna-1,4-diene-3,20-dione |
| 21-(acetoxy)-9,11β-dichloropregna-1,4,16-triene-3,20-dione | 21-(acetyloxy)-9,11β-dichloro-17a-hydroxy-16β-methoxy-D-homo-17-oxapregna-1,4-diene-3,20-dione |
| 21-(acetyloxy)-9,11β-dibromopregna-1,4,16-triene-3,20-dione | 21-(acetyloxy)-9,11β-dibromo-17a-hydroxy-16β-methoxy-D-homo-17-oxapregna-1,4-diene-3,20-dione |
| 21-(acetyloxy)-9-bromo-11β-chloropregna-1,4,16-triene-3,20-dione | 21-(acetyloxy)-9-bromo-11β-chloro-17a-hydroxy-16β-methoxy-D-homo-17-oxapregna-1,4-diene-3,20-dione |

What is claimed is:

1. A steroid having the formula,

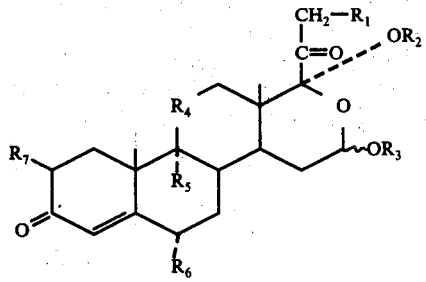

or the 1,2-dehydro derivative thereof; wherein $R_1$ is hydrogen,

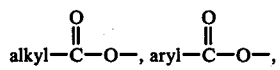

halogen or hydroxy; $R_2$ is hydrogen or alkyl; $R_3$ is alkyl; $R_4$ is carbonyl, β-hydroxymethylene, β-chloromethylene or β-bromomethylene; $R_5$ is hydrogen, fluorine, chlorine or bromine; $R_6$ is hydrogen, fluorine or methyl; and $R_7$ is hydrogen, chlorine or bromine; with the proviso that when $R_1$ is hydroxy, $R_2$ is alkyl; and with the further proviso that when $R_2$ is alkyl, it is the same alkyl group as $R_3$; wherein aryl is phenyl or phenyl substituted with one or two alkyl, alkoxy or halogen groups; and alkyl and alkoxy are groups having 1 to 10 carbon atoms.

2. A steroid in accordance with claim 1 wherein $R_6$ and $R_7$ are hydrogen.

3. A steroid in accordance with claim 2 wherein $R_2$ is hydrogen.

4. A steroid in accordance with claim 2 wherein $R_2$ is alkyl.

5. A steroid in accordance with claim 2 wherein $R_4$ is β-hydroxymethylene.

6. A steroid in accordance with claim 1 wherein $R_1$ is

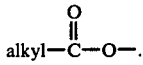

7. A steroid in accordance with claim 1 wherein $R_1$ is halogen.

8. A steroid in accordance with claim 1 wherein $R_1$ is hydroxy.

9. A steroid in accordance with claim 1 having the formula

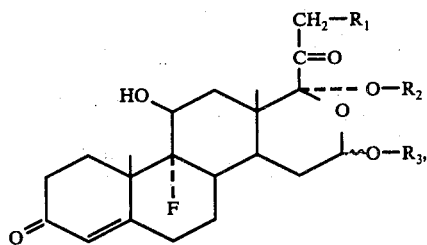

or the 1,2-dehydro derivative thereof.

10. A steroid in accordance with claim 9, 21-(acetyloxy)-9-fluoro-11β,17a-dihydroxy-16β-methoxy-D-homo-17-oxapregna-1,4-diene-3,20-dione.

11. A steroid in accordance with claim 9, 21-chloro-9-fluoro-11β,17a-dihydroxy-16β-methoxy-D-homo-17-oxapregn-4-ene-3,20-dione.

12. A steroid in accordance with claim 9, 21-(acetyloxy)-9-fluoro-11β,17a-dihydroxy-16β-methoxy-D-homo-17-oxapregn-4-ene-3,20-dione.

13. A steroid in accordance with claim 9, 21-(acetyloxy)-16β,17a-diethoxy-9-fluoro-11β-hydroxy-D-homo-17-oxapregn-4-ene-3,20-dione.

14. A steroid in accordance with claim 9, 16β,17a-diethoxy-9-fluoro-11β,21-dihydroxy-D-homo-17-oxapregn-4-ene-3,20-dione.

15. A steroid in accordance with claim 9, 21-chloro-16β,17a-diethoxy-9-fluoro-11β-hydroxy-D-homo-17-oxapregn-4-ene-3,20-dione.

16. A steroid in accordance with claim 9, 21-chloro-16β-ethoxy-9-fluoro-11β,17a-dihydroxy-D-homo-17-oxapregna-1,4-diene-3,20-dione.

17. A steroid in accordance with claim 9, 21-chloro-9-fluoro-11β,17a-dihydroxy-16β-methoxy-D-homo-17-oxapregna-1,4-diene-3,20-dione.

18. A steroid in accordance with claim 9, 21-chloro-16β,17a-diethoxy-9-fluoro-11β-hydroxy-D-homo-17-oxapregna-1,4-diene-3,20-dione.

19. A steroid in accordance with claim 9, 21-chloro-9-fluoro-11β-hydroxy-16β,17a-dimethoxy-D-homo-17-oxapregna-1,4-diene-3,20-dione.

20. A steroid in accordance with claim 9, 21-(acetyloxy)-16β-ethoxy-9-fluoro-11β,17a-dihydroxy-D-homo-17-oxapregna-1,4-diene-3,20-dione.

21. A steroid in accordance with claim 9, 21-(acetyloxy)-16β,17a-diethoxy-9-fluoro-11β-hydroxy-D-homo-17-oxapregna-1,4-diene-3,20-dione.

22. A steroid in accordance with claim 9, 21-(acetyloxy)-9-fluoro-11β-hydroxy-16β,17a-dimethoxy-D-homo-17-oxapregna-1,4-diene-3,20-dione.

23. A steroid in accordance with claim 9, 21-chloro-16β-(1,1-dimethylethoxy)-9-fluoro-11β,17a-dihydroxy-D-homo-17-oxapregna-1,4-diene-3,20-dione.

24. A steroid in accordance with claim 9, 21-chloro-9-fluoro-11β-hydroxy-16β,17a-bis-(1-methylethoxy)-D-homo-17-oxapregna-1,4-diene-3,20-dione.

25. A steroid in accordance with claim 9, 21-chloro-9-fluoro-11β,17a-dihydroxy-16β-(1-methylethoxy)-D-homo-17-oxapregna-1,4-diene-3,20-dione.

* * * * *